(12) United States Patent
Williams et al.

(10) Patent No.: US 6,635,205 B2
(45) Date of Patent: *Oct. 21, 2003

(54) METHOD OF MANUFACTURING A CATAMENIAL/TAMPON DEVICE

(75) Inventors: Karla E Williams, Westwood, NJ (US); Rosemary F. Knuth, Congers, NY (US); Keith Edgett, Ramsey, NJ (US)

(73) Assignee: Playtex Products, Inc., Westport, CT (US)

( * ) Notice: Subject to any disclaimer, the term of this patent is extended or adjusted under 35 U.S.C. 154(b) by 182 days.

This patent is subject to a terminal disclaimer.

(21) Appl. No.: 09/878,511

(22) Filed: Jun. 11, 2001

(65) Prior Publication Data

US 2001/0028126 A1 Oct. 11, 2001

Related U.S. Application Data

(63) Continuation-in-part of application No. 09/399,654, filed on Sep. 21, 1999, now Pat. No. 6,248,274.

(51) Int. Cl.[7] .............................. D01D 5/06; D01F 2/10
(52) U.S. Cl. ....................... 264/103; 264/188; 264/211
(58) Field of Search ............................... 264/103, 188, 264/211

(56) References Cited

U.S. PATENT DOCUMENTS

| | | |
|---|---|---|
| 3,222,857 A | 12/1965 | Keyser |
| 3,339,357 A | 9/1967 | Marzocchi et al. |
| 3,474,616 A | 10/1969 | Zeisberg |
| 3,479,811 A | 11/1969 | Walters |
| 4,525,410 A | 6/1985 | Hagiwara et al. |
| 4,744,374 A | 5/1988 | Deffeves et al. |
| 4,826,497 A | 5/1989 | Marcus et al. ............... 604/359 |
| 4,911,898 A | 3/1990 | Hagiwara et al. |
| 4,911,899 A | 3/1990 | Hagiwara et al. |
| 5,364,380 A | 11/1994 | Tanzer et al. |
| 5,413,747 A | 5/1995 | Akers et al. ................. 264/211 |
| 5,428,948 A | 7/1995 | Ballhausen et al. |
| 5,457,950 A | 10/1995 | Ballhausen et al. |
| 5,460,881 A | 10/1995 | Hsu |
| 5,489,469 A | 2/1996 | Kobayashi et al. |
| 5,492,759 A | 2/1996 | Eriksson et al. |

FOREIGN PATENT DOCUMENTS

| | | |
|---|---|---|
| WO | WO 00/50098 A1 | 8/2000 |

*Primary Examiner*—Leo B. Tentoni
(74) *Attorney, Agent, or Firm*—Ohlandt, Greeley, Ruggiero & Perle, LLP

(57) ABSTRACT

The present invention provides a method for making an odor adsorbent tampon or related catamenial device. The method of the present invention includes the steps of forming a plurality of fibers, preferably by extrusion, and impregnating or urging into or inserting into the interstices of the fibers with one or more odor adsorbent materials while the process of forming the fibers is being performed. Thereafter, the plurality of fibers so formed are suitably and conventionally brought together to produce the finished device. Preferably, the one or more odor adsorbent materials is in liquid form and/or is naturally sourced.

13 Claims, 1 Drawing Sheet

METHOD OF MANUFACTURING A CATAMENIAL/TAMPON DEVICE

RELATED APPLICATION

This application is a continuation-in-part of U.S. patent application Ser. No. 09/399,654 filed on Sep. 21, 1999, now U.S. Pat. No. 6,248,274.

BACKGROUND OF THE INVENTION

1. Field of the Invention

The present invention relates to a method of manufacturing catamenial and tampon devices and, in particular, to a method which completely simplifies the conventional way of making an odor absorbent tampon.

2. Description of the Prior Art

The assignee, as well as a number of other makers of catamenial or tampon devices, currently market such devices which achieve odor adsorbency in non-deodorant catamenials or tampons. However, such adsorbency is typically provided by a strip comprising an odor adsorbing material adhered to a non-woven material with an acrylic binder. The odor adsorbent strip is fed into the tampon forming machine along with rayon pads. The pads and strip are then formed into the tampon pledget. Alternately, the odor adsorbing material is mixed with water (a suspension aid, e.g., Veegum may be used) and added as a slurry directly to the rayon pads prior to their formation into the tampon pledget.

It will be manifest to those skilled in this art that the addition of the odor adsorbent strip, as described, is costly. A less costly alternative to the addition of a strip is to apply the odor adsorbent material, for example, as a powder or in a slurry, directly to the tampon. However, this and similar lower cost alternatives are technically more difficult since they involve additional steps in the tampon forming process and have the potential for leaving residue that would accumulate on the tampon forming equipment.

What has been discovered or recognized is that the technically difficult and problematic techniques, which are currently followed as possible alternatives for the addition of the odor adsorbent strip, can be avoided by adopting a more efficient method.

As background for an understanding and appreciation of the present invention, reference may be made to the following U.S. Pat. Nos. 3,222,857; 3,339,357; 3,479,811; and 5,460,881. Although these relate in general to processes and apparatus for producing impregnated fiber materials of one kind or another, they fail to recognize what is inherent in the concept of the present invention; that a significant advantage is obtained by uniquely combining with the usual steps involved in producing a catamenial/tampon device, the step, at the beginning of the process, of embedding the odor adsorbent material in the matrix fibers while these fibers are being formed or processed. In other words, prior to the actual formation or fabrication of the tampon pledget, the odor adsorbent material is placed or merged in the pledget's fibers.

A substantial benefit that results from the unique step described is that there is uniform distribution of the adsorbent within the finished catamenial/tampon product. This result contrasts sharply with that obtained by use of conventional processes.

SUMMARY OF THE INVENTION

It is an object of the present invention to simplify the process or method of making an odor adsorbent tampon.

It is another object of the present invention to provide such a process or method where one or more finely divided odor adsorbent materials, whether in particulate or liquid form, are incorporated directly into the fibers during the process of forming such fibers.

It is still another object of the present invention to provide such a process or method where the fibers having the one or more odor adsorbent materials are subsequently used to form a catamenial/tampon device.

It is a further object of the present invention to provide such a process or method where the one or more odor adsorbent materials is in liquid form.

It is still a further object of the present invention to provide such a process or method where the one or more odor adsorbent materials is naturally sourced.

The fundamental features of the present invention reside in a method of manufacturing a catamenial/tampon device and the product produced by that method. The method, briefly stated, includes the steps of forming a plurality of fibers, preferably by extrusion, and impregnating or urging into or inserting into the interstices of the fibers, one or more odor adsorbent materials while the process of forming the fibers is being performed. Thereafter, the plurality of fibers so formed are suitably and conventionally brought together to produce the finished device. Preferably, the one or more odor adsorbent materials is in liquid form and/or is naturally sourced.

Other and further objects, advantages and features of the present invention will be understood by reference to the following specification in conjunction with the annexed drawings, wherein like parts have been given like numbers.

DETAILED DESCRIPTION OF THE INVENTION

Figure 1:
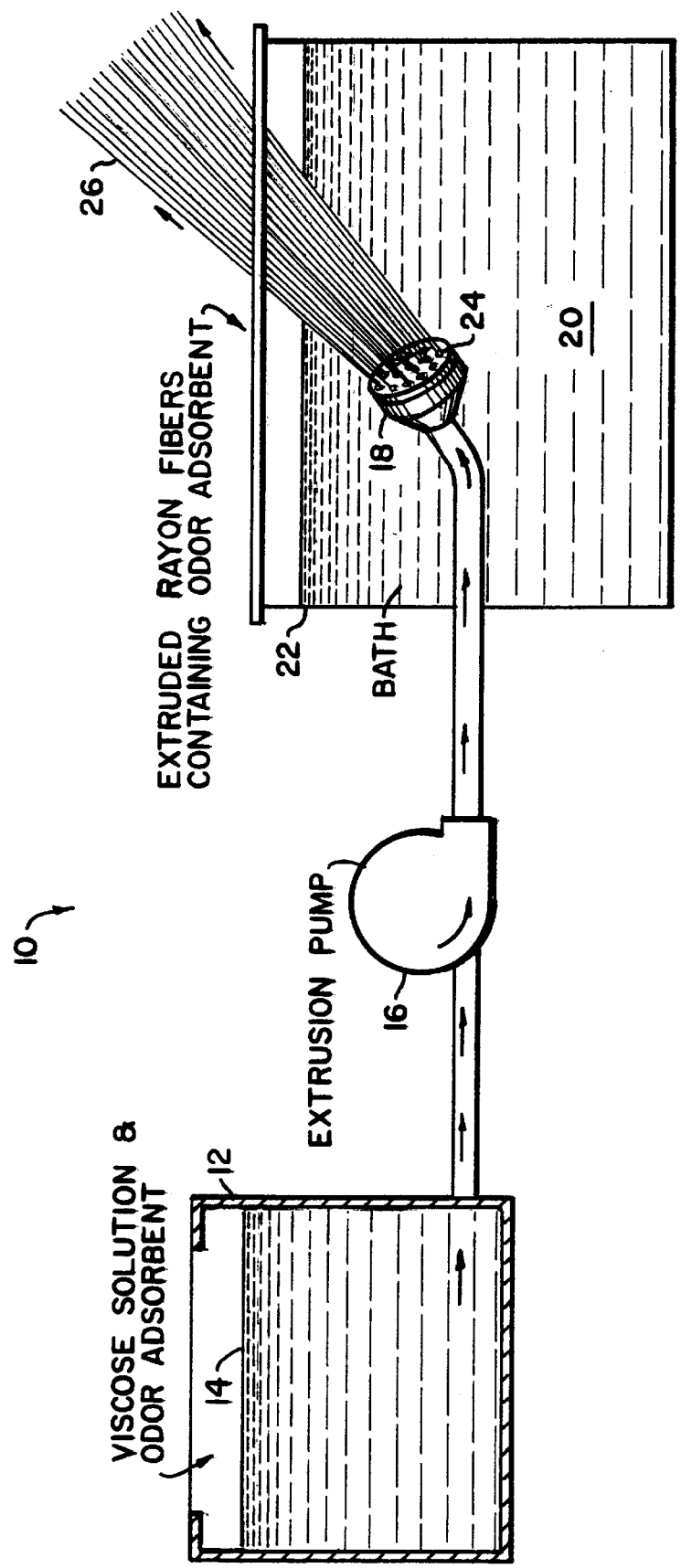
FIG. 1 is a perspective view of the apparatus deployed in the practice of the present invention.

Referring to FIG. 1, there is provided a preferred arrangement for practicing the method of the present invention. Particularly, FIG. 1 illustrates the novel process by which fibers for use in tampons are impregnated with or have urged into or inserted into the interstices thereof one or more odor adsorbent materials, as the fibers are being generated. This method is different than having the pledget or the like formed from the fibers and impregnating the fibers with odor adsorbent material at a later stage of manufacturing.

Shown in FIG. 1 is an apparatus generally represented by reference numeral 10 by which the basic objective of the present invention is realized. Apparatus 10 has a tank or vessel 12 that contains a viscose solution 14 to which one or more odor adsorbent materials has been added. Viscose solution 14 is pumped by a conventional device 16, such as an extrusion pump, connected to tank 12 and a second tank 22 to an emitting device 18 which is disposed in an acid bath 20 contained in tank 22. Preferably, emitting device 18 has a plurality of apertures 24.

Operation of extrusion pump 16 produces sufficient pressure to force viscose solution 14 or the like through apertures 24 and into acid bath 20, thereby providing individual rayon fibers 26 that can be further conventionally processed to produce the catamenial product.

The one or more odor adsorbent materials may be any material that is capable of adsorbing odors. Such materials may essentially have no particulate matter, as in a liquid, or an amount of fine particulate matter, as in a zeolite, such that it can be incorporated into solution that forms the fiber. It is preferred that the one or more odor adsorbent materials be in liquid form and/or naturally sourced.

The one or more odor adsorbent materials that can be used in the process of the present invention may include, for example, one or more glycerins, glycerin compounds, aldehydes, natural oils, solutions of soluble natural compounds, natural plant and herb extracts, naturally occurring deodorizing actives, acids, bases, oxidants, chelating agents, esters, masking agents, sensory receptor alterants, oxidizing agents, biological agents, surfactants, surface active polymers, or any mixtures thereof.

Suitable glycerin compounds for use in the present invention include, for example, glycolic acid, glycerin stearate, glycerin monolaurate, glycerin monoalkyl ether, or any combinations thereof.

Aldehydes or aldehyde compositions containing an aldehyde selected from one class (Class A) and an aldehyde selected from a second class (Class B), have been found to have remarkable deodorant properties, clearly superior to those of each class of aldehyde compositions taken individually. The aldehyde technology consists of using materials of low vapor pressure. Efficacy is thought to be the result of a combination of various methods of neutralizing odors, which include, chemical reaction with malodorant molecules, slow evaporation of the functional ingredients, and a partial masking effect. In the presence of malodor, the reaction product has been chemically altered so that one of the following occurs: (1) the new molecule is more volatile and quickly evaporates, (2) the new molecule is much larger and virtually non-volatile so the nose cannot detect its presence, or (3) the new molecule, being chemically different, has a more pleasant odor profile.

Suitable Class A aldehydes, may include, for example, one or more acyclic aliphatic aldehydes, non-terpenic aliphatic aldehydes, non-terpenic alicyclic aldehydes, terpenic aldehydes, aliphatic aldehydes substituted by an aromatic group, bifunctional aldehydes, or any mixtures thereof. More specifically, suitable Class A aldehydes may include, for example, decanal, lilal, tripal, or any mixtures thereof.

Suitable Class B aldehydes may include, for example, one or more aldehydes having an unsaturation carried by the carbon in the alpha position of the aldehyde function, aldehydes having an unsaturation in the alpha position of the aldehyde function conjugated with an aromatic ring, aldehydes having the function carried by an aromatic ring, or any mixtures thereof. For example, the Class B aldehydes may include alpha-, betaunsaturated aldehydes including beta-aryl substituted alpha-, beta- unsaturated aldehydes, aromatic aldehydes, or any mixtures thereof. More specifically, suitable Class B aldehydes may include, for example, citral, benzaldehyde, vanillin, or any mixtures thereof.

The aldehyde compositions may contain three or more aldehydes, as long as each of the two classes are represented. Preferably, the aldehydes of Class A and Class B are present in a proportion of about 80/20 to about 20/80.

Natural oils may be used as a suitable odor absorbent material in the present invention. The natural oils can have the effect of suppressing the malodorant molecules and imparting a pleasant odor, which overpowers the malodor. By way of example, a suitable natural oil for use in the present invention is white cedar leaf oil.

Solutions of any soluble natural compounds capable of malodor counteraction may also be used in the present invention. One example of such a soluble natural compound is chlorophyll.

Natural plant and herb extracts may also be used as malodor counteractant materials in the present invention. By way of example, suitable natural extracts may include green tea extract, Glade® "Neutralizer" (proprietary mixture of plant and herb extracts), or any mixtures thereof.

Naturally occurring deodorizing active materials may also be used in the present invention to counteract malodors. Suitable naturally occurring deodorizing actives include, for example, farnesol, phenoxyethanol, alkali rhodanides, linalol, citronellol, geraniol, phenethyl alcohol, or any mixtures thereof.

One or more acids may be used as malodor counteractants that act to neutralize basic components of the malodor. Suitable acids include, for example, citric acid, acetic acid, other organic acids that are safe for use, or any mixtures thereof.

One or more bases may be used as malodor counteractants that act to neutralize acid components of the malodor. Suitable bases include, for example, ammonia, triethanolamine, or any mixtures thereof.

One or more oxidants that react with sulfide-containing compounds to reduce malodors may also be used in the present invention. By way of example, suitable oxidants may include ascorbic acid or other known oxidating materials.

One or more chelating agents that react with any metal components and reduce or eliminate malodors may be used in the present invention. Suitable chelating agents may include, for example, ascorbic acid or other known chelating agents, such as, for example, EDTA.

Certain esters having reactive double bonds have been found to have a quasi-universal ability of abating malodors. Suitable ester compounds for use in the present invention include, for example, NEUTROAIR® (a mixture of geranyl crotonate and dihexyl fumarate) or METAZENE® (lauryl methacrylate).

Masking agents may be used as a malodor counteractant material in the present invention. Any agent capable of masking malodor may be used. However, typically, for example, a perfume or fragrance is used to mask or hide the malodor.

Compounds that are capable of altering the body's sensory receptors may also be used in the present invention. Malodor counteractants share common areas of receptor sites with many known malodor-causing chemicals. Given sufficient concentration in the atmosphere, the malodor counteractants interact with the receptor proteins and render them unavailable to malodors. Therefore, without interaction of the malodor with the receptors, no perception of the malodor by the nose is possible. By way of example, Veilex® (proprietary ingredients), produced by BBA, is such a malodor counteractant suitable for use in the present invention.

One or more oxidizing agents may be used as malodor counteractants that act to oxidize components of the malodor. Any suitable oxidizing agent may be used in the absorbent article of the present invention that is safe for use, such as, for example, hydrogen peroxide.

One or more biological agents may be used as malodor counteractants in the absorbent article of the present invention. Suitable biological agents include, for example, bacterial spores, enzymes, or any mixtures thereof.

One or more surfactants may be used as malodor counteractants in the absorbent article of the present invention. Suitable surfactants include, for example, anionic, nonionic, cationic, zwitterionic, silicone, or any mixtures thereof.

One or more surface-active polymers may be used as malodor counteractants in the absorbent article of the present invention. Suitable surface-active polymers include, for example, acrylate polymers.

From the description herewith provided of the present invention, it will be understood that the great advantage and benefit of incorporating the odor adsorbent material in the first instance directly into the fibers eliminates both the potential for dusting during processing of catamenial devices and the need for binders and/or thickening agents that are normally used in the conventional methods. As previously noted, the method has been made more effective because the impregnation step normally performed at the end stage of the manufacturing procedures has already been accomplished, thereby eliminating the residue accumulation problem previously discussed.

The final step in the method of the present invention is a conventional step of bringing together a plurality of the individual fibers 26 formed and treated as described, so as to produce the finished product. Thus the already impregnated fibers, whether they be of rayon or other materials, are brought together as rayon and/or cotton fiber have conventionally been brought together in known tampons and in other catamenial devices. This bringing together can be accomplished by conventional non-weaving techniques.

Although in this description of the present invention a preferred embodiment thereof is specifically illustrated, it will be appreciated that alternate techniques may be exploited for achieving the essential objective of incorporating the odor adsorbent material in the fibers while such fibers are being formed or processed.

The present invention having been thus described with particular reference to the preferred forms thereof, it will be obvious that various changes and modifications may be made therein without departing from the spirit and scope of the invention as defined in the appended claims.

Wherefore we claim:

1. A method of manufacturing a catamenial/tampon product comprising the steps of:
   (a) forming a plurality of fibers and, during the process of forming, incorporating in the fibers one or more naturally sourced odor adsorbent materials selected from the group consisting of: glycerin, glycerin compound, aldehyde, natural oil, solution of soluble natural compound, natural plant and herb extract, naturally occurring deodorizing active, acid, base, oxidant, chelating agent, ester, masking agent, sensory receptor alterant, oxidizing agent, biological agent, surfactant, surface-active polymer, and any mixtures thereof; and
   (b) forming the plurality of fibers into the catamenial/tampon product.

2. The method of claim 1, wherein the one or more odor adsorbent materials is in liquid form.

3. A method of manufacturing a catamenial/tampon product comprising the steps of:
   (a) forming a plurality of fibers from a viscose solution and, during the process of forming, incorporating in the fibers one or more odor adsorbent materials selected from the group consisting of: glycerin, glycerin compound, aldehyde, natural oil, solution of soluble natural compound, natural plant and herb extract, naturally occurring deodorizing active, acid, base, oxidant, chelating agent, ester, masking agent, sensory receptor alterant, oxidizing agent, biological agent, surfactant, surface-active polymer, and any mixtures thereof; and
   (b) forming the plurality of fibers into the catamenial/tampon product.

4. The method of claim 3, further comprising a step of pumping the viscose solution containing the one or more odor adsorbent materials to a device for extruding the fibers, whereby the one or more odor adsorbent materials is incorporated in the fibers.

5. The method of claim 4, wherein the one or more odor adsorbent materials are added to the viscose solution prior to extrusion of the viscose solution.

6. The method of claim 3, wherein the fibers are rayon.

7. The method of claim 3, wherein the one or more odor adsorbent materials is in liquid form.

8. The method of claim 3, wherein the one or more odor adsorbent materials is naturally sourced.

9. The method of claim 7, wherein the one or more odor adsorbent materials is naturally sourced.

10. A method of manufacturing a catamenial/tampon product comprising the steps of:
    (a) forming a plurality of fibers and, during the process of forming, incorporating in the fibers one or more odor adsorbent materials selected from the group consisting of: glycerin, glycerin compound, aldehyde, natural oil, solution of soluble natural compound, natural plant and herb extract, naturally occurring deodorizing active, base, oxidant, ester, masking agent, sensory receptor alterant, oxidizing agent, biological agent, and any mixtures thereof; and
    (b) forming the plurality of fibers into the catamenial/tampon product.

11. The method of claim 10, wherein the one or more odor adsorbent materials is in liquid form.

12. The method of claim 10, wherein the one or more odor adsorbent materials is naturally sourced.

13. The method of claim 11, wherein the one or more odor adsorbent materials is naturally sourced.

* * * * *